United States Patent [19]

Yotam et al.

[11] Patent Number: 4,595,495
[45] Date of Patent: Jun. 17, 1986

[54] PROGRAMMABLE SOLVENT DELIVERY SYSTEM AND PROCESS

[75] Inventors: Reuben Yotam; Joseph G. Carleton, both of Palo Alto, Calif.

[73] Assignee: Eldex Laboratories, Inc., San Carlos, Calif.

[21] Appl. No.: 704,201

[22] Filed: Feb. 22, 1985

[51] Int. Cl.$^4$ .............................................. B01D 15/08
[52] U.S. Cl. .................... 210/101; 210/198.2; 417/18
[58] Field of Search ............... 210/101, 143, 198.2; 417/18

[56] References Cited

U.S. PATENT DOCUMENTS

| | | | |
|---|---|---|---|
| 4,045,343 | 8/1977 | Achener et al. | 210/101 |
| 4,128,476 | 12/1978 | Rock | 210/101 |
| 4,311,586 | 1/1982 | Baldwin et al. | 210/198.2 |
| 4,492,524 | 1/1985 | Koch et al. | 417/18 |

Primary Examiner—John Adee
Attorney, Agent, or Firm—Willis E. Higgins

[57] ABSTRACT

A solvent delivery system (10) has first and second pistons (92, 94) and cylinders (58, 68) connected to first and second cams (110, 112). The cams (110, 112) each have a ramped portion (150, 162) and an abrupt step (152, 164). The first cylinder (58) is connected to solenoid valves (44, 46, 48) to fill the first cylinder with solvent components during movement of cam follower (104) along ramped portion (150) of the first cam (110). Spring (140) urges the first piston (92) forward into first cylinder (58). Movement of the cam follower (104) over the step (152) of the cam (110) moves the piston (92) forward abruptly to force the solvent components from cylinder (58) into second cylinder (68). Spring (178) urges piston (94) back in cylinder (68). The second cam (112) is reversed relative to first cam (110). Movement of cam follower (106) over abrupt step (164) of second cam (112) moves second piston (94) back abruptly in cylinder (68) to receive and mix the solvent components in the cylinder (68). Movement of cam follower (106) along ramped portion (162) of cam (112) moves piston (94) forward to force the solvent mixture from the second cylinder (68). A third piston (96) and cylinder (74) has a lesser volume than the first and second cylinders (58, 68). A third cam (114) and cam follower (108) move the third piston (96) back in cylinder (74) when second piston (94) moves forward in second cylinder (68). The second cylinder (68) delivers the solvent mixture to outlet (80) and fills third cylinder (74) while second piston (94) moves forward and third piston (96) moves back. The third cylinder (74) delivers the solvent mixture to outlet (80) while the third piston moves forward, the solvent component fills the first cylinder (58) and the first piston (92) and cylinder (58) fill the second cylinder (68). Check valves (60, 72, 78) prevent backflow in the system.

24 Claims, 17 Drawing Figures

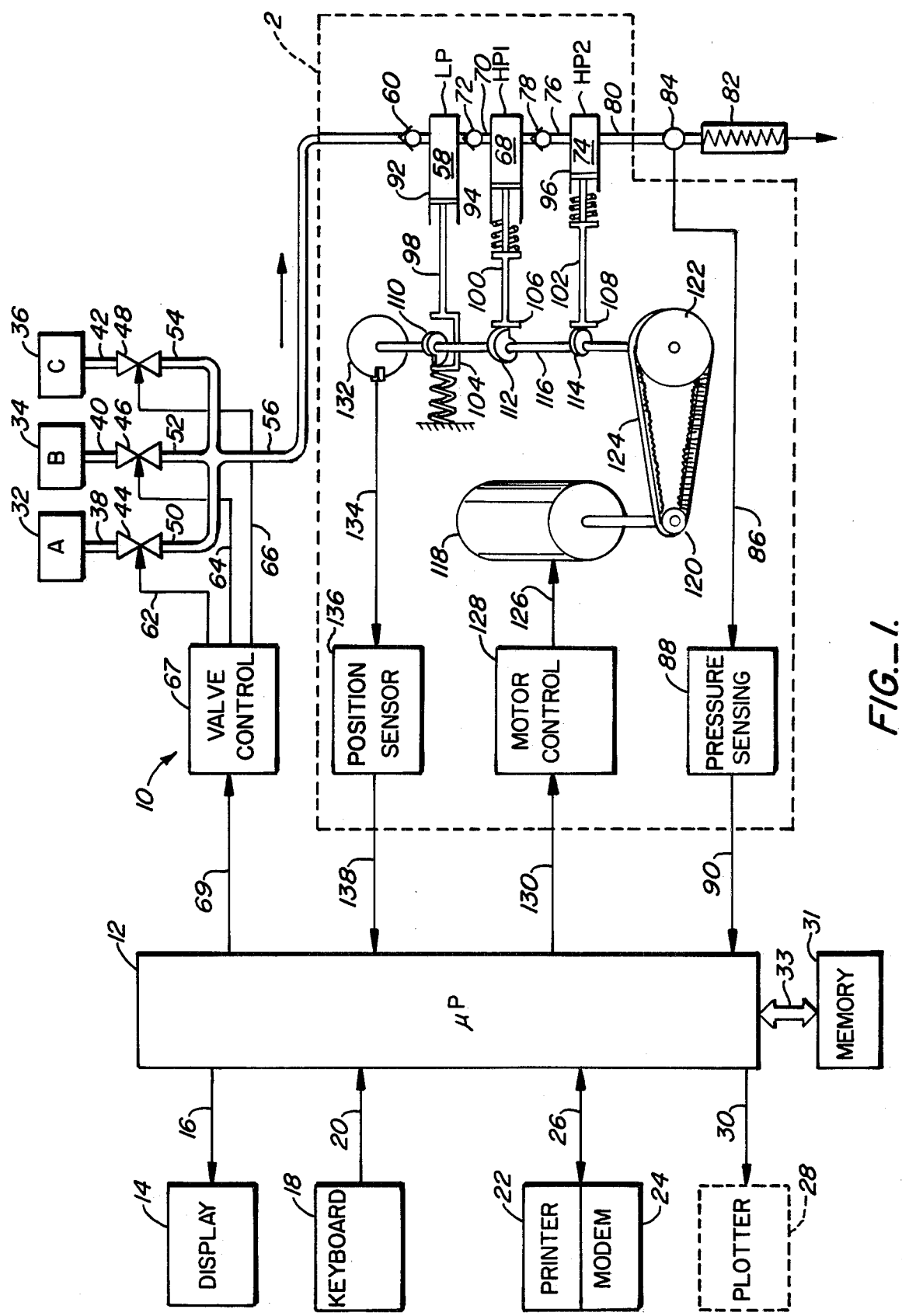
FIG._1.

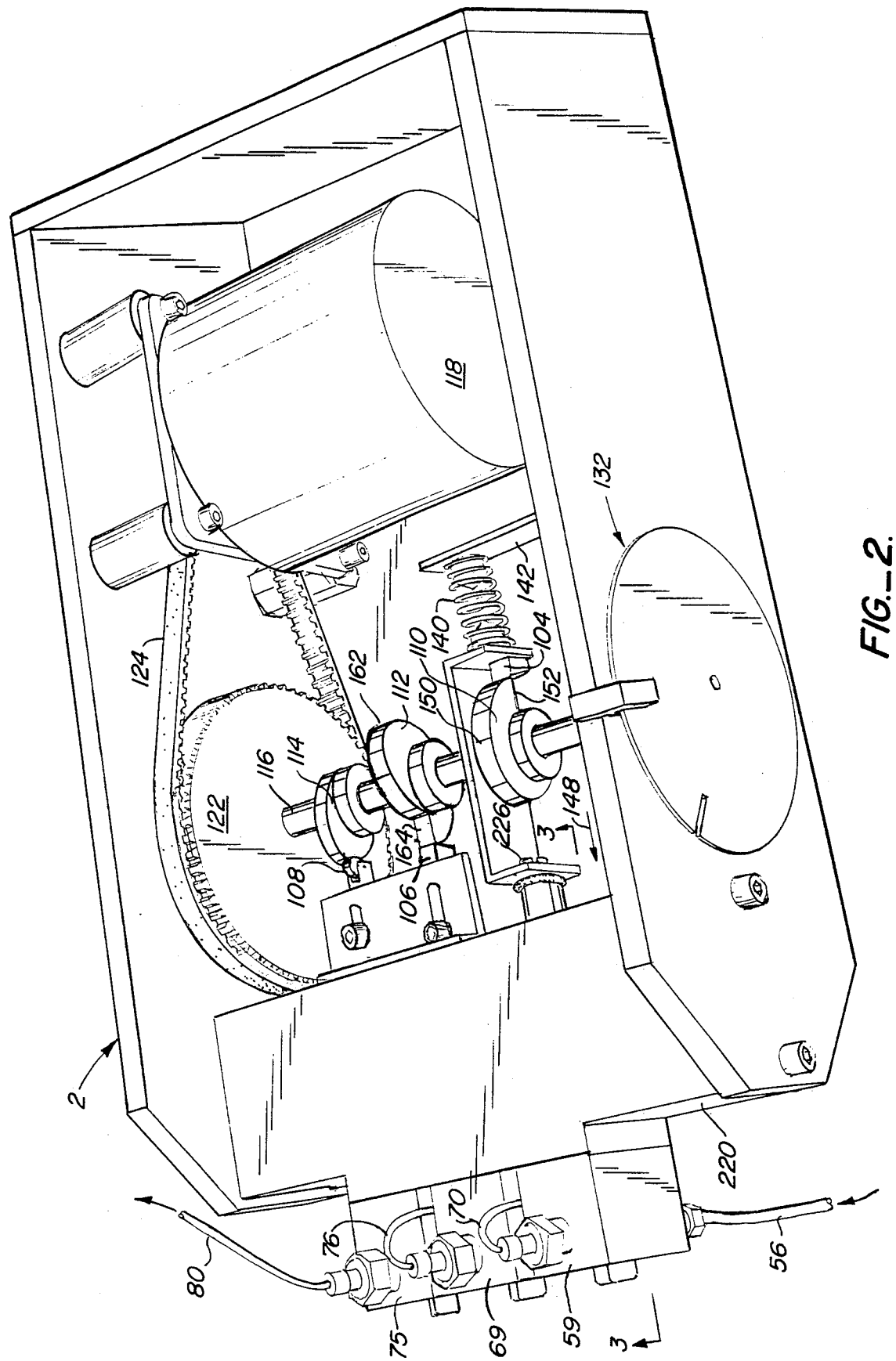
FIG._2.

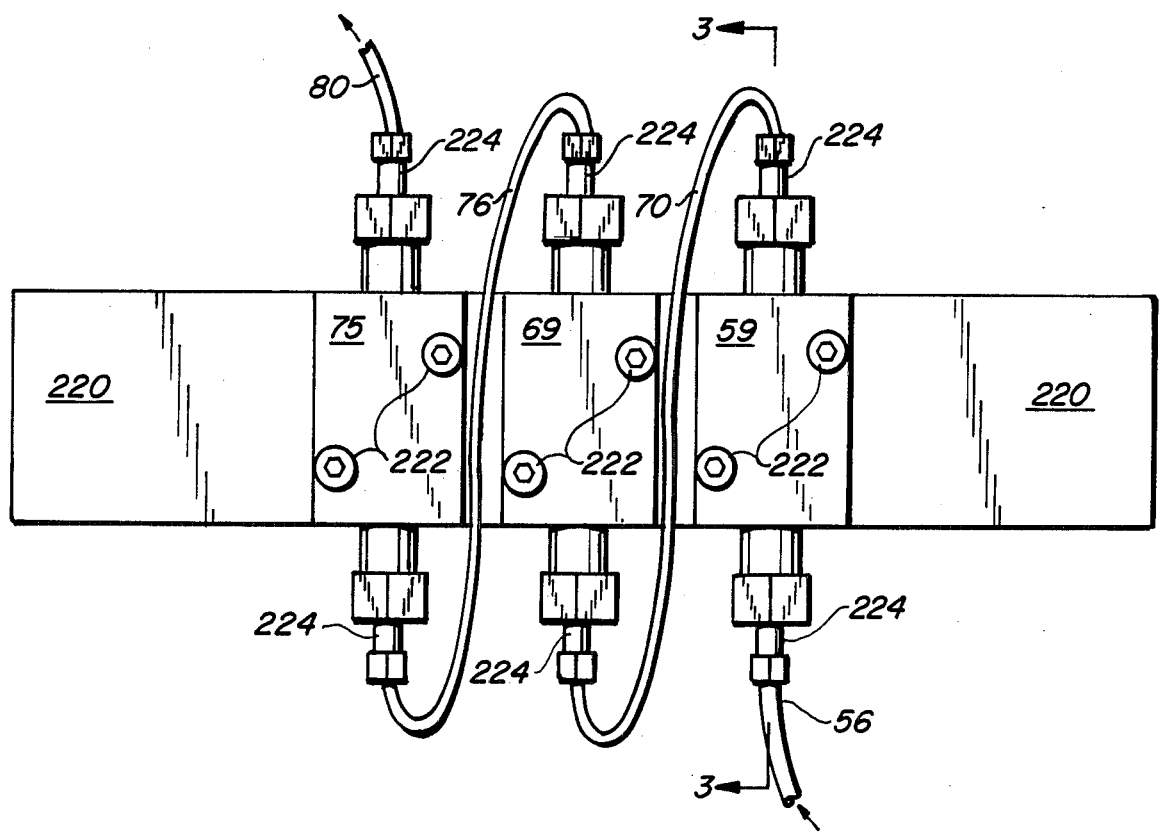
FIG.—7.
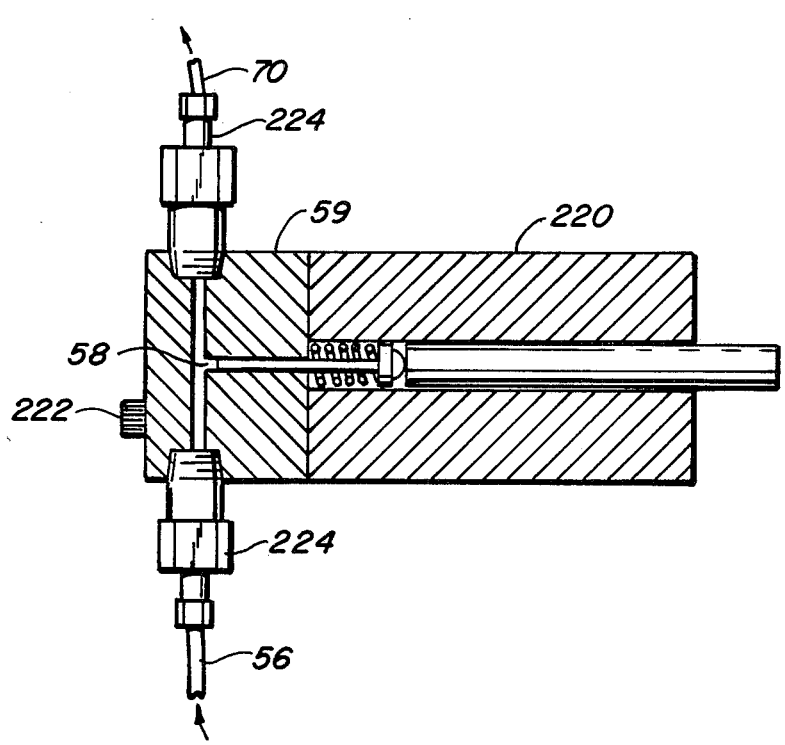
FIG.—3.

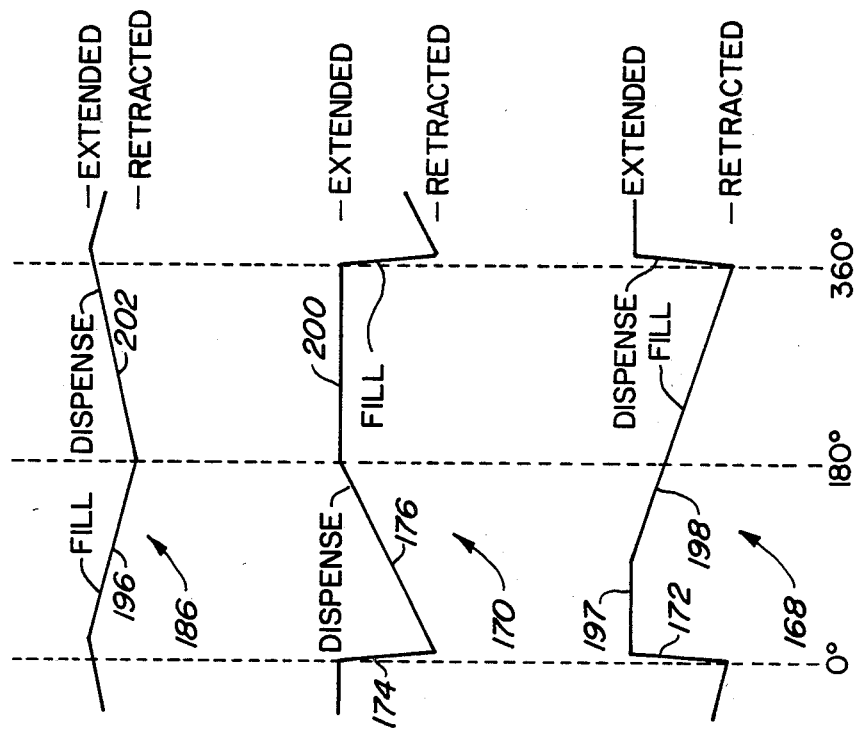
FIG._5.
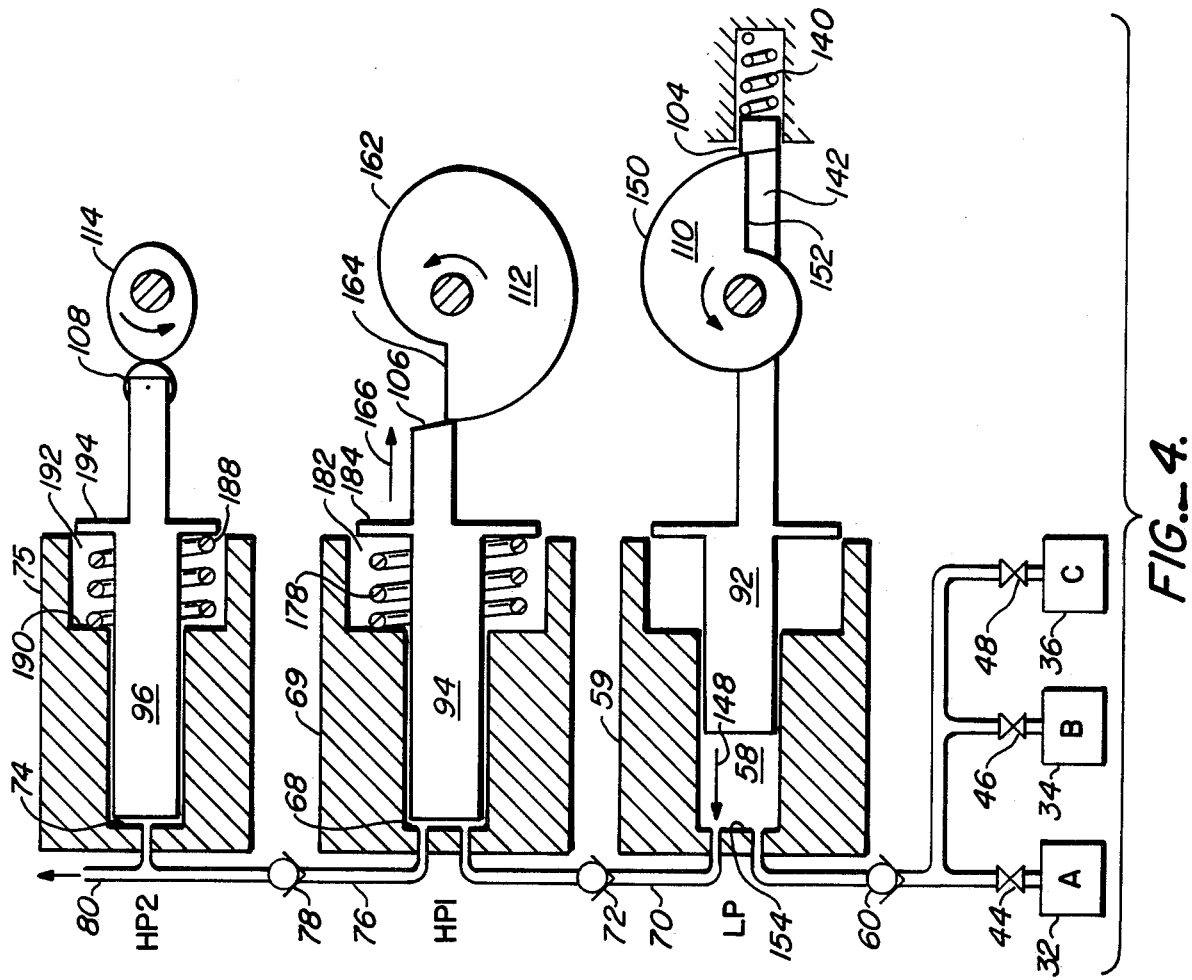
FIG._4.

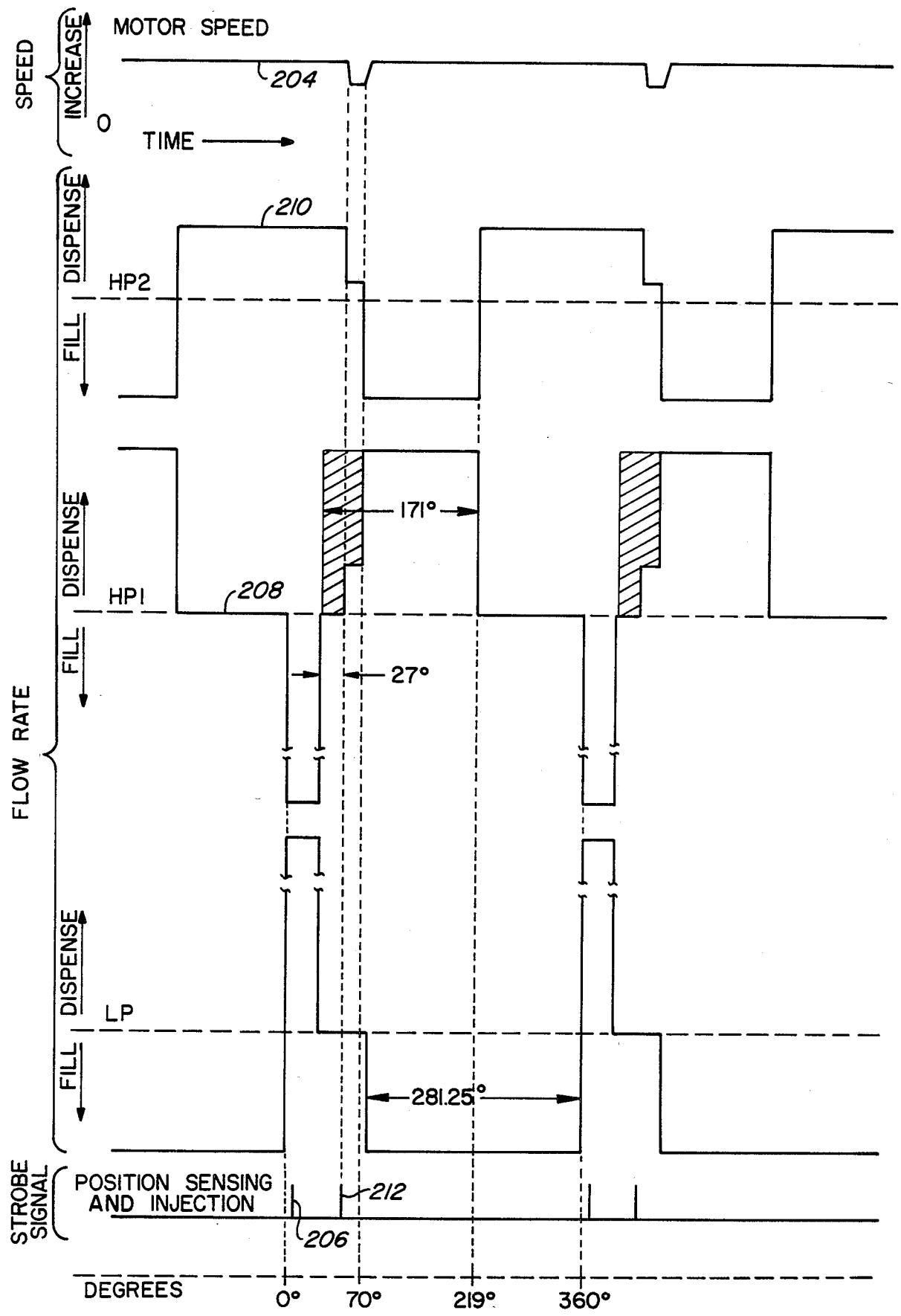
FIG._6.

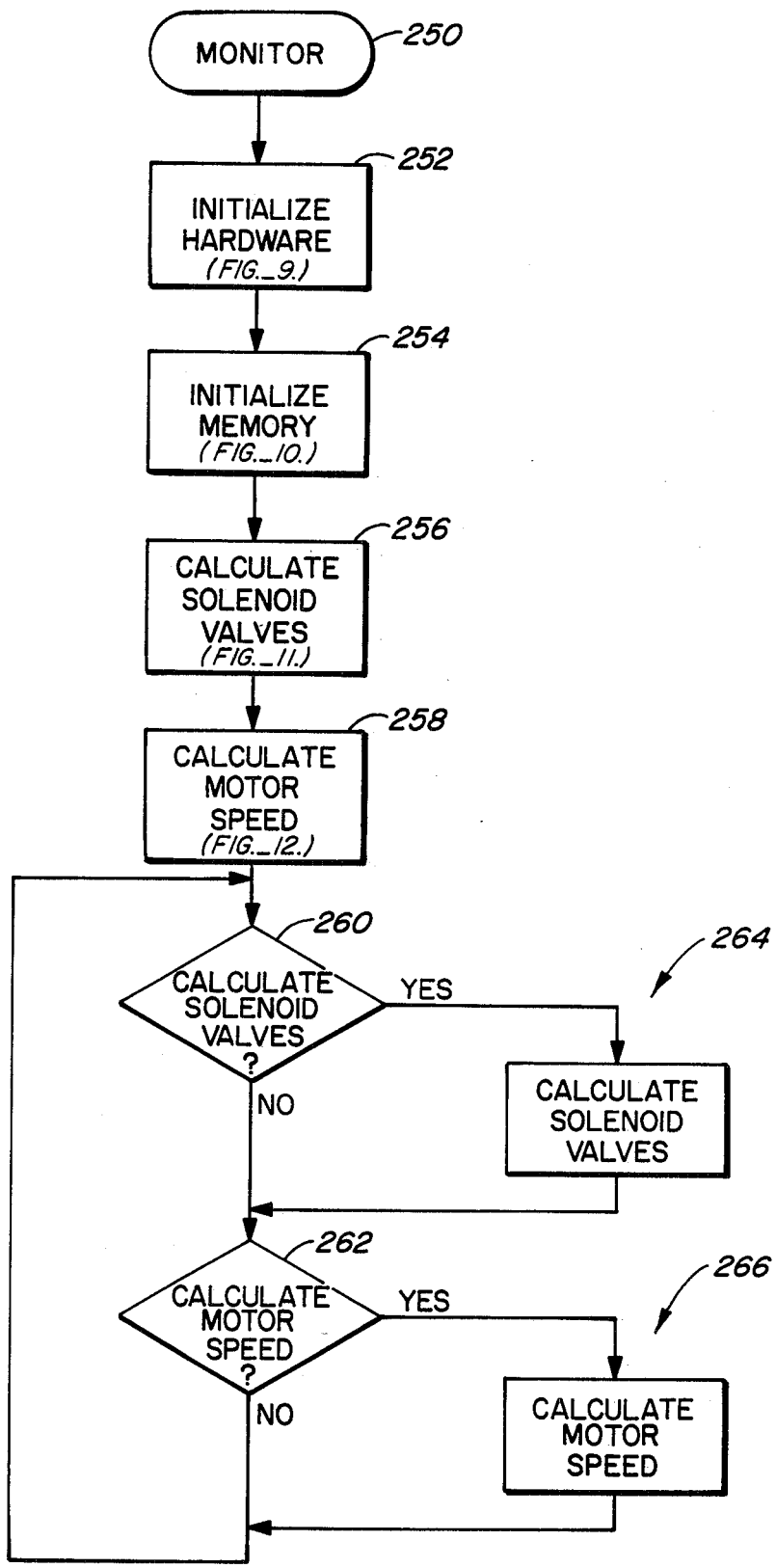
FIG._8.

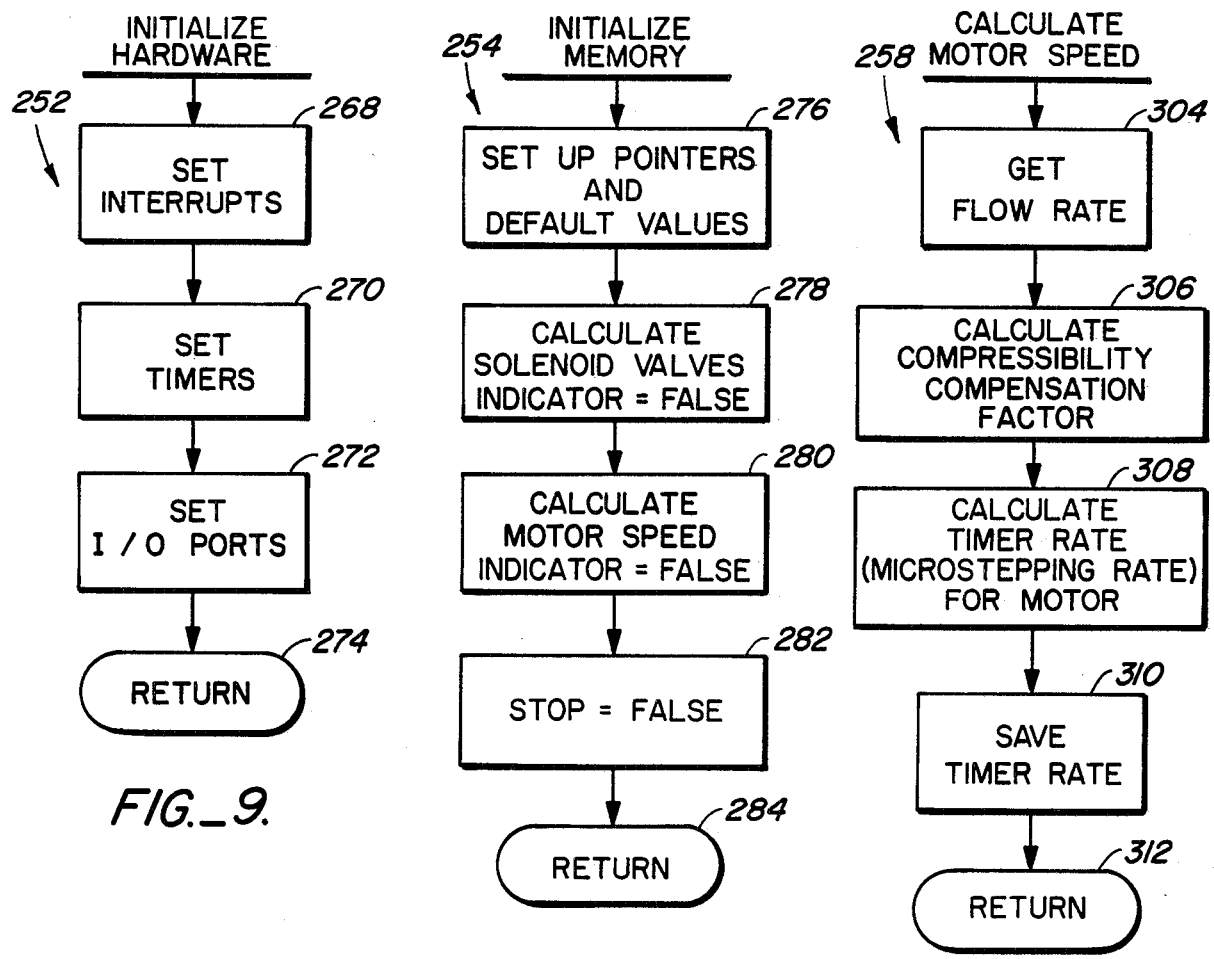
FIG._9.  FIG._10.  FIG._12.
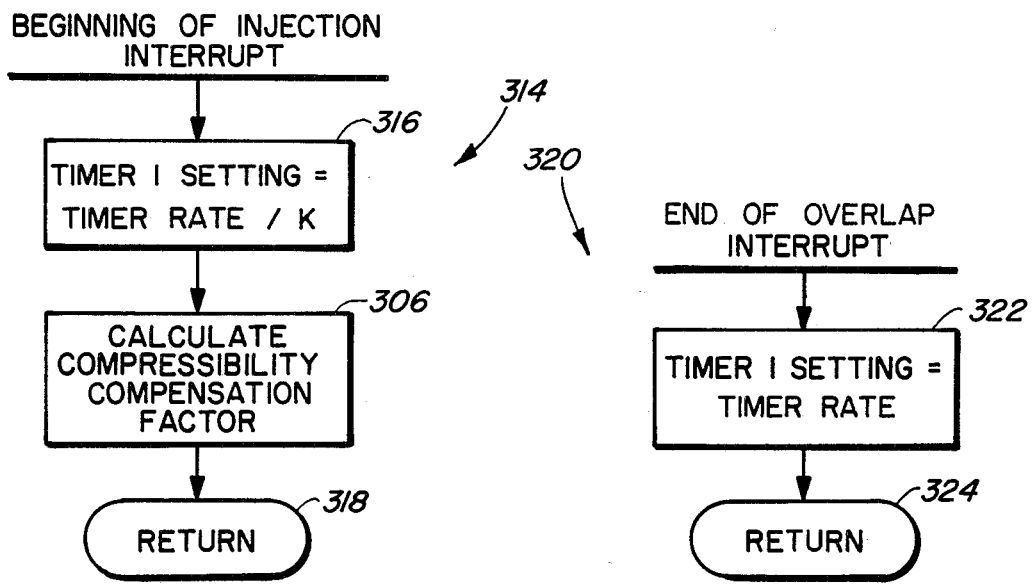
FIG._13.  FIG._14.

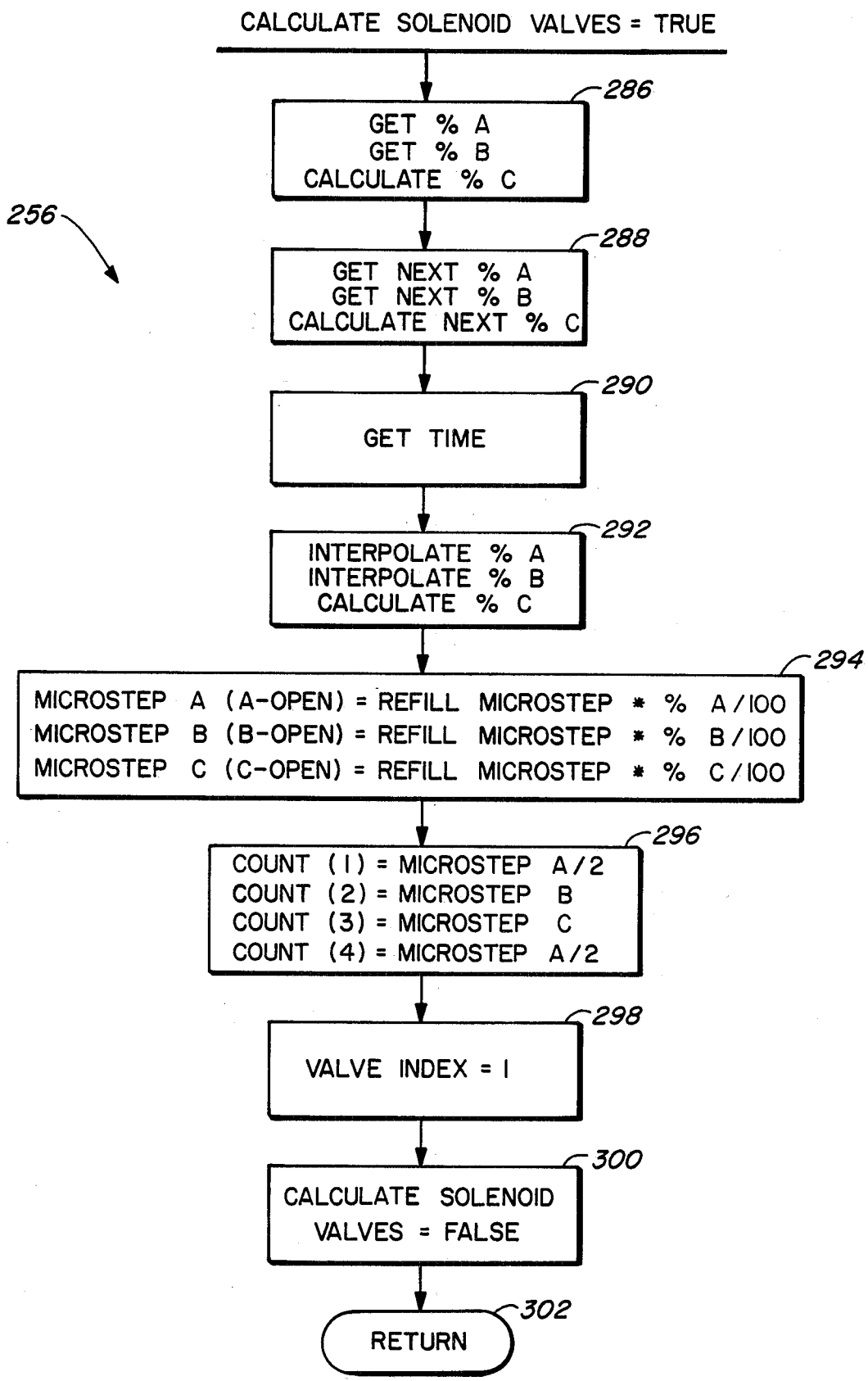
FIG._11.

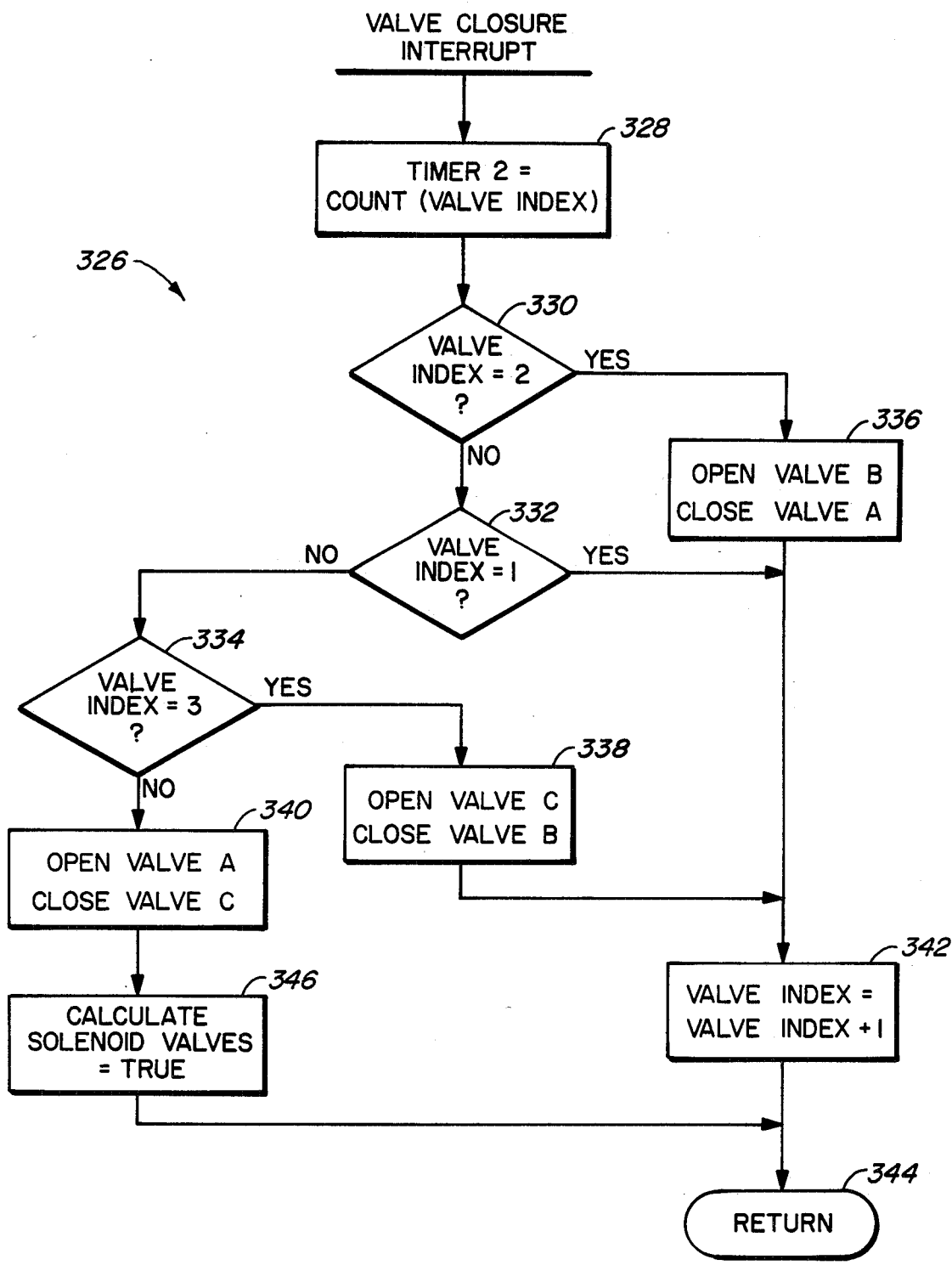
FIG._15.

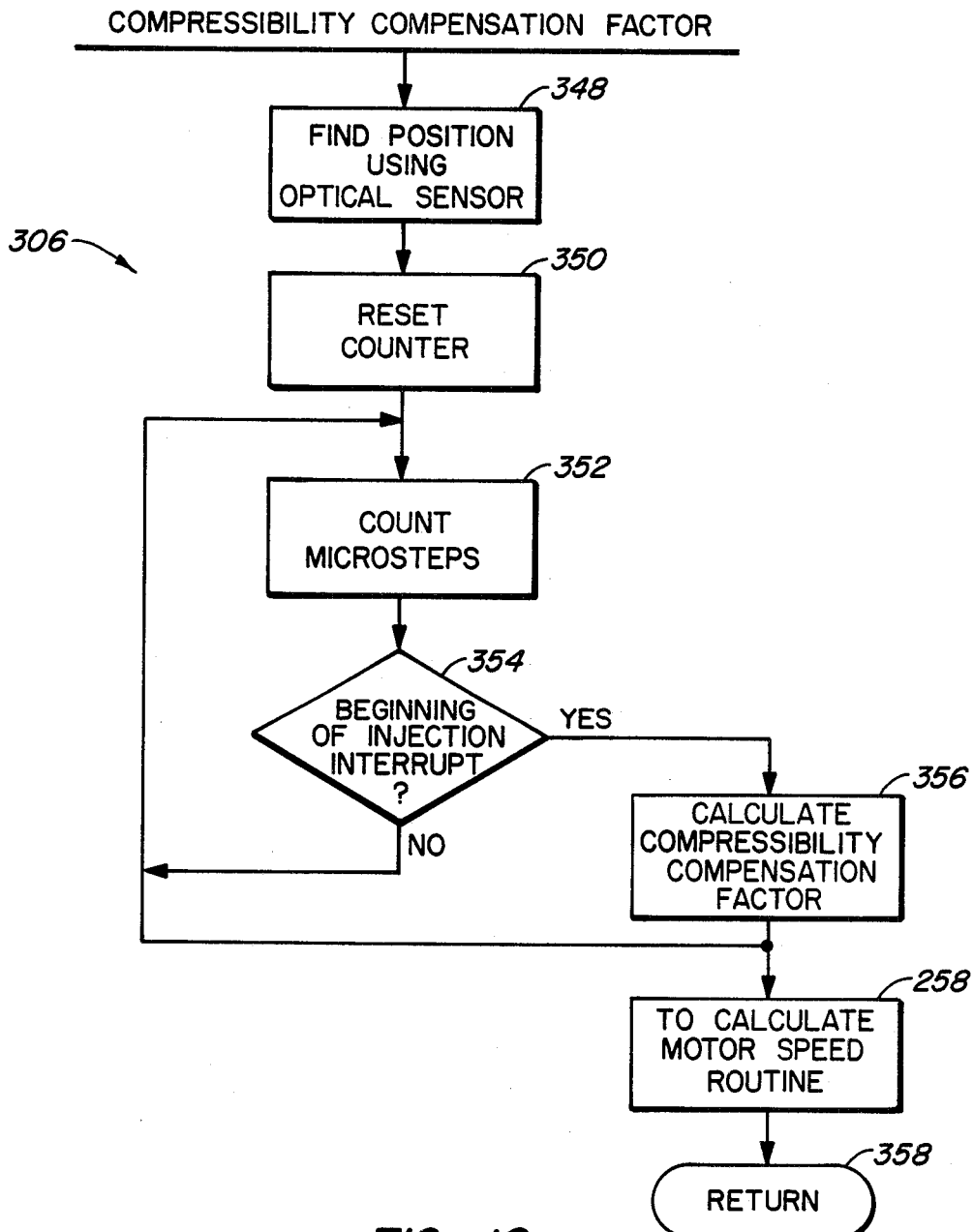
FIG._16.
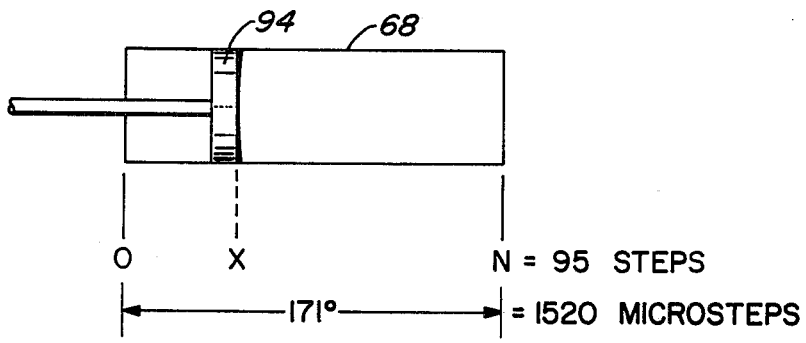
FIG._17.

PROGRAMMABLE SOLVENT DELIVERY SYSTEM AND PROCESS

BACKGROUND OF THE INVENTION

1. Field of the Invention

This invention relates to a pump, valve and electronic system and a process which will deliver a liquid solvent mixture at elevated pressures for liquid chromatography and similar applications. More particularly, it relates to such a system and process which will vary the proportions of the solvent mixture components and solvent flow rate smoothly at pressures of up to about 6,000 psi.

2. Description of the Prior Art

A variety of solvent delivery systems for supplying solvent mixtures for liquid chromatography and related applications are known in the art. Two basic approaches are employed in the art, both using two pistons. The first approach uses one piston to deliver liquid to the column while the second piston is used to refill the solvents from liquid containers. A sudden reversal of one piston injects solvent solution from a low pressure cylinder into a high pressure cylinder. The second approach uses the two pistons in such a way that at least one piston is always dispensing liquid to the chromatographic column. One piston is used for a part of the pump cycle to refill solvents from the liquid containers and for another part of the pump cycle to dispense liquid into the column and to refill the second piston. While the first piston is refilling the second piston is dispensing liquid to the column. A drawback of the first approach is that the injection step produces undesirable pressure pulsing in the system, necessitating the use of a pulse damping reservoir. Such a reservoir increases system volume, and a low system volume is desired for rapid solvent composition changes. A drawback of the second approach is that it requires a mixer in addition to the two reverse pistons, which also increases system volume and contributes to system complexity.

Examples of prior art solvent delivery systems are disclosed in the following issued U.S. patents: U.S. Pat. Nos. 4,137,011, issued Jan. 30, 1979 to Rock; 4,173,437, issued Nov. 6, 1979 to Leka et al. and 4,260,342, issued April 7, 1981 to Leka et al. Another example of a prior art solvent delivery system is described in commonly assigned pending application Ser. No. 561,219, filed Dec. 14, 1983, by Keith S. Clark, entitled "Solvent Proportioning and Mixing Apparatus and System". A further indication of the state of the art is contained in the following references: Savage, M., "Accuracy and Reproducibility in a Two-Pump Gradient HPLC", American Laboratory, May 1979, pp. 49-57; Conlon, R. D. et al., "An Advanced LC System", American Laboratory, Sept. 1982; Schwartz, H. et al., "A Dual Syringe LC Solvent Delivery System for Use with Microbore Columns", American Laboratory, October 1984, pp. 43-58; Fielding, R. M., "A Low-Cost Automated Step-Gradient HPLC System", LC, Vol. 2, No. 7, pp. 532-535. Commercially available solvent delivery systems are available under the following designations: "Spectroflow 430" from Kratos Analytical Instruments, Ramsey, N.J. "miniPump VS" from LDC/Milton Roy, Riviera Beach, Fla.; "Varian Model 5560" from Varian Associates, Palo Alto, Calif.; "SP 8700" from Spectra-Physics, Mountain View, Calif.; "Waters Model 510" from Millipore; "HP 1090" from Hewlett Packard, Palo Alto, Calif.; "Model 112" from Beckman Instruments, Fullerton, Calif.; and "Series 4LC" from Perkin-Elmer Corp., Norwalk, Conn.

Due to system complexity necessary to achieve high performance, the high performance systems in the above examples, such as the Perkin-Elmer Model 4LC, are quite expensive. While the art of these solvent delivery systems is a highly sophisticated one, there is a substantial need to achieve such high performance at a significantly reduced cost.

SUMMARY OF THE INVENTION

Accordingly, it is an object of the invention to provide a high performance solvent delivery system which eliminates pressure pulsing without requiring the use of a pressure damper reservoir.

It is a further object of the invention to provide such a solvent delivery system with reversed pistons which does not require the use of a separate mixer.

It is still another object of the invention to provide such a solvent delivery system in which automatic compensation for solvent compressibility is made at the high pressure portion of the pumping cycle.

It is a still further object of the invention to provide such a solvent delivery system which will deliver a solvent mixture at a predetermined flow rate through its whole operating cycle.

It is another object of this invention to provide such a high performance programmable solvent delivery system which utilizes only a single stepper motor to drive the system.

The attainment of these and related objects may be achieved through use of the novel high performance programmable solvent delivery system herein disclosed. A solvent delivery system in accordance with this invention has first and second pistons and cylinders operatively coupled to first and second drive means, such as cams and cam followers. The first and second cams each have a ramped portion and abrupt step. The first cylinder is connected to a plurality of solvent component inlets to fill the first cylinder with the solvent components during movement of the first cam follower along the ramped portion of the first cam. A first biasing means is connected to urge the first piston forward into the first cylinder. Movement of the first cam follower over the abrupt step of the first cam allows the first piston to move forward abruptly to force the solvent components from the first cylinder into the second cylinder. A second biasing means is connected to urge the second piston back in the second cylinder. The second cam is reversely arranged relative to the first cam, so that movement of the second cam follower over the abrupt step of the second cam allows the second piston to move back in the second cylinder to allow the solvent components to enter and be mixed to form a solvent mixture in the second cylinder. Movement of the second cam follower along the ramped portion of the second cam moves the second piston forward into the second cylinder to force the solvent mixture from the second cylinder. The system includes a third piston and cylinder, with the third cylinder having a lesser volume than the first cylinder and the second cylinder. A third drive means, such as another cam and cam follower, is coupled to reciprocate the third piston in the third cylinder. The third cam is configured and positioned relative to the second cam so that the third piston moves back in the third cylinder when the second piston moves forward in the second cylinder. The second cylinder and the third cylinder are connected so that the second cylinder delivers the solvent mixture to a desired location, such as a chromatographic column connected to the system, and fills the third cylinder while the second piston moves forward in the second cylinder and the third piston moves back in the third cylinder. The third cylinder delivers the solvent mixture while the third piston moves forward in the third system, the solvent component sources fill the first cylinder and the first piston and cylinder fill the second cylinder. In a preferred form of the invention, there is also an overlap when both the second piston and the third piston are moving forward and delivering the solvent mixture to the column. First, second and third backflow prevention means, such as check valves are provided to prevent backflow in the system. The first check valve is connected between the plurality of solvent component sources and the first cylinder. The second check valve is connected between the first cylinder and the second cylinder. The third check valve is connected between the second cylinder and the third cylinder. In a preferred form of the invention, the first, second and third cams are mounted on a common shaft and driven by a single rotary drive, such as a stepper motor.

A solvent delivery system configured in accordance with this invention mixes and delivers a multiple component solvent mixture without requiring the use of a separate mixer or a pressure damper reservoir to eliminate pressure pulsing. The programmable solvent delivery system of this invention will deliver a solvent mixture at a predetermined flow rate through its whole operating cycle, as a result of the sequential operation of the three pistons and cylinders in the above manner.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIG. 1 is a block diagram of a programmable solvent delivery system in accordance with the invention.

FIG. 2 is a perspective view of a portion 2 of the solvent delivery system shown in FIG. 1.

FIG. 3 is a cross-section view, taken along the line 3—3 in FIG. 2.

FIG. 4 is a schematic diagram of a portion of the system shown in FIGS. 1 and 2.

FIG. 5 is a timing diagram useful for understanding operation of the system portion shown in FIG. 3.

FIG. 6 is another timing diagram showing the first derivative of the timing diagram of FIG. 5 and additional timing, useful for a further understanding of the FIG. 1-2 system operation.

FIG. 7 is a front view of a part of the system portion shown in FIG. 2.

FIGS. 8-16 are flow charts of software used with the system of FIG. 1.

FIG. 17 is a schematic representation of a portion of the system shown in FIG. 1, useful for understanding operation of the system.

DETAILED DESCRIPTION OF THE INVENTION

Turning now to the drawings, more particularly to FIG. 1, there is shown a programmable solvent delivery system 10 in accordance with the invention. The system 10 includes a microprocessor controller 12, which may be implemented with a control oriented microprocessor integrated circuit, such as a COPS420 or 421 integrated circuit, obtainable from National Semiconductor Corporation, Santa Clara, Calif., one of the F387X microprocessor integrated circuit controller family, available from Fairchild, Mountain View, Calif., or an Intel 8085 microprocessor, available from Intel Corporation, Santa Clara, Calif.. An LCD or other suitable display 14 for representing alphanumerical information is connected to the microprocessor 12 by bus 16. A keyboard 18 for inputting user commands is connected to the microprocessor 12 by bus 20. A printer 22 and modem 24 are connected to the microprocessor 12 by means of an RS-232 bus 26. An optional plotter 28 is connected to the microprocessor 12 by serial line 30. A system memory 31 is connected to the microprocessor 12 by bus 33.

Three solvent sources 32, 34 and 36 are connected through tubes 38, 40, 42, solenoid valves 44, 46, 48, tubes 50, 52, 54 and 56 to an about 53 microliter low pressure cylinder 58. A check valve 60 prevents back flow from the cylinder 58. The solenoid valves 44, 46 and 48 are connected to the microprocessor 12 by control lines 62, 64 and 66. The first cylinder 58 is connected to a second about 53 microliter high pressure cylinder 68 through tube 70 and check valve 72. In practice, the first piston is preferably 1 to 2 percent larger than the second piston. The second cylinder 68 is connected to a third about 25 microliter high pressure cylinder 74 through tube 76 and check valve 78. The second and third cylinders 68 and 74 are also connected by tubes 76 and 80 to a chromatographic column 82 and to a pressure transducer 84. Pressure transducer 84 is connected by line 86 to a pressure sensing circuit 88, which is in turn connected to the microprocessor 12 by bus 90, to provide signals to the microprocessor 12 representing the pressure at the top of the column 82 and a change in pressure, which indicates the beginning of solvent injection from the second cylinder. In practice, the low pressure cylinder 58 and piston 92 develop a pressure which is sufficient to open check valve 72, but should not open check valve 78. The high pressure cylinders 68 and 74 and pistons 94 and 96 develop a pressure of up to about 6000 psi. The pistons 92, 94 and 96 are typically formed from sapphire rods, conventional for precision pumps.

Pistons 92, 94 and 96 are respectively slidably mounted for reciprocation in the first, second and third cylinders 58, 68 and 74. Shafts 98, 100 and 102 respectively connect each of the pistons 92, 94 and 96 to cam followers 104, 106 and 108, which respectively engage the cams 110, 112 and 114. The cams 110-114 are mounted on shaft 116, driven by stepper motor 118 through pulleys 120 and 122 and belt 124. Line 126 connects the stepper motor 18 to a motor controller circuit 128, which is in turn connected to the microprocessor 12 by bus 130.

An opto-slotted coupler/interrupter 132 or other suitable position sensor is connected to provide output signals on line 134 based on the position of shaft 116 to a position sensor circuit 136. The position sensor circuit 136 is connected to the microprocessor 12 by line 138.

Further details of the system 10 are provided in FIGS. 2 and 3. The cylinders 58, 68 and 74 are respectively located in cylinder bodies 59, 69 and 75. The first, or low pressure cylinder 58 has a spring 140 pushing against piston rod 142 to bias the piston 92 into the cylinder 58, in the direction indicated by arrow 148.

Cam 110 has a ramped portion 150 and an abrupt step 152. As the cam follower 104 travels along the ramped portion 150 of the cam 110, piston 92 is retracted from end 154 of the cylinder 58 to the position shown, which represents the fully retracted position of the piston 92. As the piston 92 retracts, it draws solvent from the sources 32, 34 and 36 into the cylinder 58. During retraction of the piston 92, opening the solenoid valves 44, 46 and 48 for different lengths of time during the filling of cylinder 58 will allow variation in the relative proportions of solvent components A, B and C in the cylinder 58. FIG. 3 shows the cam 110 in its position at the conclusion of travel of the cam follower 104 over the ramped portion 150, just prior to dropping over step 152. Cam 112 is mounted on the shaft 116 in opposed relationship to the cam 110. Cam follower 106 is thus at the end of its travel along ramped portion 162, just prior to dropping over step 164. As the cam followers 104 and 106 drop over their respective steps 152 and 164 on cams 110 and 112, piston 92 moves to its extended position within cylinder 58, as indicated by arrow 148, and piston 94 moves to its retracted position with respect to cylinder 68 as indicated by arrow 166. Curves 168 and 170 of the piston position timing diagrams of FIG. 4 illustrate this simultaneous action in portions 172 and 174 of the curves 168 and 170, respectively.

This rapid leftward motion of the piston 92 injects the solvent components in line 70 through check valve 72 to the cylinder 68. The transfer of liquid to the cylinder 68 takes about one-twentieth of a second. This rapid injection produces turbulent flow of the solvent components into the cylinder 68, thus assuring thorough mixing of the solvent components without the provision of a separate mixing chamber.

Portion 176 of the piston position curve 170 represents the movement of piston 94 to its extended position within cylinder 68 during the travel of cam follower 106 on ramped portion 162, which moves the piston 94 in opposition to the biasing force of spring 178 between wall 180 of chamber 182 and flange 184 of the piston 94. This movement of piston 94 into cylinder 68 supplies the mixed solvent at high pressure in line 76 through check valve 78 to cylinder 74, and at the same time, in line 80 to column 82.

As piston 94 moves into cylinder 68 to supply the solvent, rotation of cam 114 allows the piston 96 to retract within cylinder 74 as a result of the biasing force supplied by spring 188 between wall 190 of chamber 192 and flange 194 of the piston 96. Cam follower 108 moves to the right as piston 114 rotates until the piston 96 is fully retracted within cylinder 74, as indicated by portion 196 of the curve 186. During this time, the solvent is being supplied to column 82 by the piston 94 and cylinder 68, as well as filling the cylinder 74. As indicated by the portions 197 and 198 of curve 168, piston 92 remains fully extended in cylinder 58 for part of this time, and retracts during the remainder of this time period to fill the cylinder 58.

When piston 94 is fully extended into cylinder 68, it remains in this position, as indicated by portion 200 of the curve 170 while piston 92 continues to retract, as indicated by the portion 198 of curve 168, continuing the filling of cylinder 58. During this portion of the cycle, piston 96 extends within cylinder 74, to dispense the solvent mixture to column 82, as indicated by portion 202 of the curve 186. Cylinder 74 and piston 96 continue to dispense the solvent to column 82 until piston 92 is fully retracted, ready to inject the solvent components into cylinder 68 in the next cycle. Check valve 78 prevents back flow while cylinder 74 and piston 96 are dispensing the solvent.

FIG. 6 is a timing diagram showing the operation of the pistons 92, 94, 96 and the stepping motor 118. Curve 204 shows the speed of the stepping motor 118. As shown, the motor speed is reduced when both pistons 94 and 96 are dispensing simultaneously to column 82. The speed reduction is initiated by the beginning of injection signal 212, which is sensed by the pressure transducer 84. When piston 96 is fully extended into cylinder 74, the speed is increased back to the speed required by the predetermined flow rate. Line 206 represents the input signal on line 134 from the shaft position sensor 132 to the position sensor circuit 136. Curves 208 and 210 respectively represent the flow rates at cylinders 68 and 74. In these curves the positive parts represent dispensing of liquid and the negative parts represent filling of the cylinders.

Line 212 represents the beginning of injection signal on line 90. This signal is detected as a result of a pressure increase when piston 94 begins to dispense liquid to the column. This region is an overlap region because piston 96 is still dispensing to the column.

The beginning of injection is not a fixed place in the cycle. It depends of the compressibility of the solvents and the backpressure of the column. To assure always having a beginning of injection signal an overlap region of 27° is used.

Automatic compensation is made for solvent compressibility to assure constant flow at the top of the column regardless of the compressibility and backpressure of the column. The point where the overlap of dispense of liquid by both cylinders 68 and 74 begins is used to determine what percentage of the volume of the liquid is decreased in cylinder 68 prior to the beginning of injection. For a given backpressure and compressibility of the mixed solvents, the reduction in the volume of the liquid in cylinder 68 supplies the required information to be used by the microprocessor 12 in order to adjust the motor speed.

FIGS. 2, 3 and 7 show additional details of the cylinder bodies 59, 69 and 75 and pistons 58, 68 and 74 which enable the cylinder bodies and pistons to be easily interchanged and replaced. The cylinder bodies 59, 69 and 75 are attached to block 220 by screws 222. The tubes 56, 70, 76 and 80 are connected to the cylinder bodies 59, 69 and 75 by fittings 224. The check valves 60, 72, and 78 (FIG. 1) are in the lower fittings 224. Screw 226 attaches the cam follower 104 to piston 92. Screws 228 through slots 230 slidably attach cam followers 106 and 108 to their cylinder bodies 69 and 75 to engage their pistons. By disconnecting the fittings 224 and removing screws 222, 226 and 228, the cylinder bodies 59, 69, and 75 can be removed and replaced with other cylinder heads having different size cylinders and pistons, but the same external dimensions, without disturbing motor 118, pulleys 120 and 122, belt 124 or cams 110, 112 and 114. Such replacement allows the flow system 10 to handle a range of flow rates which vary by a factor of four or more, i.e., this system can handle flow rates of from about 0.01 ml/minute to about 40 ml/minute.

FIG. 8 shows a generalized flow diagram for software used to control operation of the system 10 of FIG. 1. As indicated at 250, the software specific to this system application operates under a monitor of a generalized system control program. The system 10 and its memory must be initialized when the program begins, as indicated at 252 and 254. The system and memory initialization operations are explained below in connection with FIGS. 9 and 10, respectively. After initialization, solenoid valve opening times are calculated, as indicated at 256. As previously explained, the solenoid valves 44, 46 and 48 are opened for different periods of time during the filling of cylinder 58 in order to adjust the proportion of components A, B and C in the solvent mixture delivered by the system 10. The program calculates the opening time for each solenoid valve on the basis of user entered compositions desired for the mixture. Similarly, the program then calculates a motor speed for the stepping motor 118 to give a user entered flow rate of the solvent mixture, as indicated at 258. Details on the calculation of the solenoid valve opening times and the motor speed are given in FIGS. 11 and 12, respectively, discussed below. Decision blocks 260 and 262 respectively initiate loops 264 and 266 to carry out the calculations.

FIG. 9 shows the hardware initialization subroutine 252. In this subroutine, system interrupts, system timers and system I/0 ports are set, as indicated at 268, 270 and 272, followed by a return to the main program of FIG. 8, indicated at 274.

FIG. 10 shows the subroutine 254 for initializing memory 31. Pointers and default values are set up, as indicated at 276. An indicator for calculating solenoid values and an indicator for calculating motor speed are initialized as false, shown at 278 and 280, respectively. A STOP flag is set as false, shown at 282, followed by a return to the main program at 284.

FIG. 11 shows the subroutine 256 for calculating the solenoid valve opening times. In order to understand the operation of this subroutine, certain background details of the system 10 are necessary. Time in the system 10 is measured in microsteps. There are 16 microsteps in a step, and there are 200 steps in each revolution of the stepper motor 118. One revolution of the motor therefore is 3200 microsteps. Since there are four revolutions of the motor 118 for each revolution of the cams 110, 112 and 114, there are 12,800 microsteps for each 360° of cam motion. The fill portion of each revolution of cam 110 for cylinder 58 represents 281.25° of the cam 110 rotation (see FIG. 6), which is 10,000 microsteps. The subroutine 256 begins with the calculate solenoid open times indicator set as true. The subroutine gets two of the composition percentages which have been entered by the user, and calculates the third by subtraction at 286. FIG. 11 shows getting the percentages for A and B and calculating the percentage for C, but the percentage of any component can be calculated from the user entered values for the other two. In typical use of the system 10, the user wishes to execute a solvent delivery sequence in which the composition of the solvent mixture varies with time. To do this, the user enters additional percentages for two of the components and a time for the change to the additional percentages. The system gets these subsequent percentages and time, as shown at 288 and 290. In order to obtain a smooth transition between the different percentages, the system interpolates between the sets of percentages, as shown at 292. The solvent composition percentages are converted to the number of microsteps the corresponding valve 44, 46 or 48 remains open as shown at 294. By way of example, for 10% of component A, the number of microsteps that valve 44 should remain open during a refill cycle is 10,000×10/100, or 1,000 microsteps. Four counts are set with the resulting number of microsteps for each solenoid valve 44, 46 and 48, indicated at 296. Four counts are employed because the time for the valve corresponding to the largest percentage component is divided into two portions at the beginning and end of the refill cycle. This is done so that system timing errors cause the smallest error in the amount of the component subjected to the timing errors. If a small percentage component were subjected to timing errors at the beginning and end of a refill cycle, the relative error in that component would be much greater than for a large percentage component. Components in the middle of the refill cycle are not prone to such errors. The valve index is then set to 1, the calculate valve times indicator is set to false, and the subroutine 256 returns to the main program, as shown at 298, 300 and 302.

FIG. 12 shows the subroutine 258 for calculating speed of the stepper motor 118. The subroutine begins by getting a user entered flow rate at 304. A nested calculate compressibility compensation factor subroutine 306 is executed, which will be explained below in connection with FIG. 16. The compressibility compensation factor is utilized to result in the delivery of a constant solvent volume at the top of column 82. A timer rate (microstepping rate) for delivering the user entered solvent flow rate, e.g. 2.5 ml/minute, is calculated at 308 and saved at 310, followed by a return 312 to the main program.

FIG. 13 shows a beginning of injection interrupt 314, triggered by the strobe 212 (FIG. 6). A timer 1 setting is calculated by dividing the saved timer rate at 310 (FIG. 12) by a constant K, which must be determined empirically for each system 10, as shown at 316, by varying operating speed and optimizing to minimum pulsation. The solvent compressibility factor is calculated by using the nested subroutine 306, followed by a return to the main program at 318.

An end of overlap interrupt 320 is shown in FIG. 14. The end of overlap interrupt 320 is triggered by counting a predetermined number of microsteps from shaft position signal 206, which number of microsteps represents the length of piston 96. The interrupt 320 resets the timer 1 setting to the saved timer rate at 310 (FIG. 12), indicated at 322, and returns to the main program at 324.

FIG. 15 shows a valve closure interrupt 326, which is triggered when a timer 2 has been incremented to a valve index count (see 296 in FIG. 11), shown at 328. Decision blocks 330, 332 and 334 determine which valve index count has been reached, and open and close the appropriate valves, as indicated at 336, 338, and 340. After opening and closing the valves at 336 or 338, the valve index is incremented at 342, followed by a return to the main program at 344. After opening and closing the valves at 340, the new valve operating time indicator is set as true at 346, followed by a return to the main program at 344.

Details of the compressability compensation factor subroutine 306 are shown in FIG. 16. The subroutine 306 begins by finding the position of shaft 116 by looking for strobe 206 (FIG. 6), as indicated at 348. A counter is then reset at 350, and the number of microsteps until the beginning of injection (strobe 212, FIG. 6) is counted at 352. When strobe 212 is detected, represented by decision block 354, the solvent compressibility factor is calculated at 356, followed by the motor speed calculation routine 258 and return to the main program at 358.

The algorithm for calculating the solvent compressibility factor will now be explained with the aid of FIG. 17. As indicated in FIG. 17, the cylinder 68 has a design volume of 53.33 microliter. When piston 94 moves to the right from its 0 position, it travels to a position x before solvent injection occurs, as a result of solvent compressibility. X is expressed as the number of microsteps between 0° for piston 94 and the beginning of injection, and will be different for each different solvent composition. There are N=95 steps in the length of cylinder 68, corresponding to 171° or 1520 microsteps. The actual volume of solvent dispensed by the cylinder 68 can be expressed as actual dispense =53.33 microliter ($N\times 16-(x-427)/N\times 16$), which reduces to 53.33 microliter ($(1947-x)/1520$). The quantity 427 represents the number of microsteps from strobe 206 to the 0° position of piston 94 in cylinder 68. The reciprocal of the actual dispense is defined as a motor speed increase factor to compensate for compressibility, or $1520/(1947-x)$. In practice, this factor is generally between about 1.02 and 1.07, representing a 2 to 7% increase in the stepper motor speed to compensate for solvent compressibility.

The system 10 has the capability of providing liquid gradients in which any of the liquids A, B, C can be changed between 1 and 99 percent of the total composition. Also, an isocratic solution of A, B or C can be delivered.

It should now be apparent to those skilled in the art that a novel programmable solvent delivery system capable of achieving the stated objects of the invention has been provided. A single stepper motor is utilized in the system to provide a solvent mixture at a predetermined flow rate through the entire operating cycle of the system. Pressure pulsing is eliminated without the use of a pressure damper reservoir, and the system does not require a separate mixer. The system detects solvent compressibility and compensates at the high pressure portion of the pumping cycle.

It should further be apparent to those skilled in the art that various changes in form and details of the invention as shown and described may be made. It is intended that such changes be included within the spirit and scope of the claims appended hereto.

What is claimed is:

1. A solvent delivery system, which comprises first and second pistons and cylinders operatively coupled to first and second cams and cam followers, said first and second cams each having a ramped portion and an abrupt step, said first cylinder being connected to a plurality of solvent component inlets to fill said first cylinder with the solvent components during movement of said first cam follower along the ramped portion of said first cam, a first biasing means connected to urge said first piston forward into said first cylinder, movement of said first cam follower over the abrupt step of said first cam allowing said first piston to move forward abruptly to force the solvent components from said first cylinder into said second cylinder, a second biasing means connected to urge said second piston back in said second cylinder, said second cam being reversely arranged relative to said first cam, so that movement of said second cam follower over the abrupt step of said second cam allows said second piston to move back abruptly in said second cylinder to allow the solvent components to enter and be mixed to form a solvent mixture in said second cylinder, movement of said second cam follower along the ramped portion of said second cam moving said second piston forward into said second cylinder to force the solvent mixture from said second cylinder, a third piston and cylinder, said third cylinder having a lesser volume than said first cylinder and said second cylinder, a third cam and cam follower coupled to reciprocate said third piston in said third cylinder, said third cam being configured and positioned relative to said second cam so that said third piston moves back in said third cylinder when said second piston moves forward in said second cylinder, said second cylinder and said third cylinder being connected so that said second cylinder delivers the solvent mixture to an outlet and fills said third cylinder while said second piston moves forward in said second cylinder and said third piston moves back in said third cylinder, and said third cylinder delivers the solvent mixture to the outlet while said third piston moves forward in said third cylinder, said solvent component inlets fill said first cylinder and said first piston and cylinder fill said second cylinder, and first, second and third check valves, said first check valve being connected between said plurality of solvent component inlets and said first cylinder, said second check valve being connected between said first cylinder and said second cylinder and said third check valve being connected between said second cylinder and said third cylinder.

2. The solvent delivery system of claim 1 in which said first, second and third cams are mounted on a common shaft and a stepper motor is coupled to said shaft.

3. The solvent delivery system of claim 2 additionally comprising a plurality of solenoid valves, one of said plurality of solenoid valves being connected between each of said solvent component inlets and said first cylinder.

4. The solvent delivery system of claim 3 additionally comprising a microprocessor connected to supply control signals to said plurality of solenoid valves.

5. The solvent delivery system of claim 4 in which said microprocessor is further connected to supply control signals to said stepper motor.

6. The solvent delivery system of claim 5 additionally comprising a sensor positioned to sense position of said shaft and connected to supply position input signals to said microprocessor.

7. The solvent delivery system of claim 6 additionally comprising a pressure transducer between said second and third cylinders and said outlet, said pressure transducer being connected to supply pressure input signals to said microprocessor.

8. The solvent delivey system of claim 1 in which said first piston and cylinder is configured to deliver a somewhat larger volume than said second piston and cylinder.

9. The solvent delivery system of claim 5 in which said system is configured so that said second and third pistons and cylinders overlap in providing the solvent to the outlet.

10. A solvent delivery system, which comprises first and second pistons and cylinders operatively coupled to first and second piston drive means configured to move said first and second pistons abruptly in one direction and more slowly in an opposite direction, said first cylinder being connected to a plurality of solvent component inlets to fill said first cylinder with the solvent components during movement of said first piston drive means to move said piston in its slowly moving direction, movement of said first piston drive means in its abruptly moving direction causing said first piston to move forward abruptly to force the solvent components from said first cylinder into said second cylinder, said second piston drive means being reversely arranged relative to said first piston drive means, so that movement of said second piston drive means in its abruptly moving direction causes said second piston to move back abruptly in said second cylinder to allow the solvent components to enter and be mixed to form a solvent mixture in said second cylinder, movement of said second piston drive means in its slowly moving direction moving said second piston forward into said second cylinder to force the solvent mixture from said second cylinder, a third piston and cylinder, said third cylinder having a lesser volume than said first cylinder and said second cylinder, a third piston drive means coupled to reciprocate said third piston in said third cylinder, said third piston drive means being configured relative to said second piston drive means so that said third piston moves back in said third cylinder when said second piston moves forward in said second cylinder, said second cylinder and said third cylinder being connected so that said second cylinder delivers the solvent mixture to an outlet and fills said third cylinder while said second piston moves forward in said second cylinder and said third piston moves back in said third cylinder, and said third cylinder delivers the solvent mixture to the outlet while said third piston moves forward in said third cylinder, said solvent component inlets fill said first cylinder and said first piston and cylinder fill said second cylinder, and first, second and third backflow prevention means, said first backflow prevention means being connected between said plurality of solvent component inlets and said first cylinder, said second backflow prevention means being connected between said first cylinder and said second cylinder and said third backflow prevention means being connected between said second cylinder and said third cylinder.

11. The solvent delivery system of claim 10 in which said first, second and third piston drive means are mounted on a common shaft powered by a single motive means coupled to said shaft.

12. The solvent delivery system of claim 11 additionally comprising a plurality of controllable valves, one of said plurality of controllable valves being connected between each of said solvent component inlets and said first cylinder.

13. The solvent delivery system of claim 12 additionally comprising a microprocessor connected to supply control signals to said plurality of controllable valves.

14. The solvent delivery system of claim 13 in which said microprocessor is further connected to supply control signals to said motive means.

15. The solvent delivery system of claim 14 additionally comprising a sensor positioned to sense position of said shaft and connected to supply position input signals to said microprocessor.

16. The solvent delivery system of claim 15 additionally comprising a pressure transducer between said second and third cylinders and said outlet, said pressure transducer being connected to supply pressure input signals to said microprocessor.

17. The solvent delivery system of claim 10 in which said first piston and cylinder is configured to deliver a somewhat larger volume than said second piston and cylinder.

18. The solvent delivery system of claim 10 in which said system is configured so that said second and third pistons and cylinders overlap in providing the solvent to the outlet.

19. A process for delivering a solvent mixture, which comprises drawing a plurality of solvent components for the mixture from a plurality of solvent component inlets into a first cylinder, abruptly injecting the solvent components into a second cylinder to mix the components in the second cylinder, forcing the resulting solvent mixture out of the second cylinder to supply a first portion of the solvent mixture to an outlet for the solvent mixture and a second portion of the solvent mixture to a third cylinder, and forcing the second portion of the solvent mixture from the third cylinder to supply the second portion of the solvent mixture to the outlet while drawing the solvent components into the first cylinder and injecting the solvent components from the first cylinder into the second cylinder.

20. The process of claim 19 additionally comprising the step of opening the controllable valves for each solvent component inlet for different lengths of time during the step of drawing the solvent components into the first cylinder to vary the composition of the solvent mixture.

21. The process of claim 19 additionally comprising the step of sensing solvent pressure while delivering the solvent mixture to the outlet and using the sensed pressure to compensate for solvent compressibility.

22. The process of claim 21 in which the sensed pressure is used to compensate for solvent compressibility by reducing an amount of force applied to the solvent mixture in the second and third cylinders to force the solvent mixture from the second and third cylinders to the outlet during an interval in which the second and third cylinders both supply the solvent mixture to the outlet.

23. The process of claim 19 in which the first cylinder delivers a somewhat larger volume of solvent components than the solvent mixture delivered by the second cylinder.

24. The process of claim 19 in which the second and third pistons and cylinders overlap in providing the solvent to the outlet.

* * * * *